(12) United States Patent
Yamashita et al.

(10) Patent No.: US 10,859,523 B2
(45) Date of Patent: Dec. 8, 2020

(54) GAS SENSOR

(71) Applicant: NGK SPARK PLUG CO., LTD., Nagoya (JP)

(72) Inventors: Masahiro Yamashita, Komaki (JP); Shoji Kitanoya, Kasugai (JP); Masaya Watanabe, Komaki (JP); Yusuke Matsukura, Nagoya (JP); Daisuke Ichikawa, Minokamo (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 176 days.

(21) Appl. No.: 16/122,964

(22) Filed: Sep. 6, 2018

(65) Prior Publication Data

US 2019/0086351 A1    Mar. 21, 2019

(30) Foreign Application Priority Data

Sep. 15, 2017 (JP) ................... 2017-177554
Apr. 17, 2018 (JP) ................... 2018-078996

(51) Int. Cl.
| | |
|---|---|
| *G01N 27/18* | (2006.01) |
| *G01N 25/18* | (2006.01) |
| *G01N 27/12* | (2006.01) |
| *G01N 27/407* | (2006.01) |
| *G01N 33/00* | (2006.01) |

(52) U.S. Cl.
CPC ............. *G01N 27/18* (2013.01); *G01N 25/18* (2013.01); *G01N 27/12* (2013.01); *G01N 27/407* (2013.01); *G01N 33/005* (2013.01)

(58) Field of Classification Search
CPC ........ G01N 27/18; G01N 25/18; G01N 27/12; G01N 27/407; G01N 33/005; G01N 33/006; G01N 27/4071; G01N 27/4074; G01N 27/4077; G01N 27/4078
See application file for complete search history.

(56) References Cited

U.S. PATENT DOCUMENTS

2015/0226688 A1* 8/2015 Watanabe ............... G01N 27/18
73/31.05
2018/0292338 A1* 10/2018 Liu ......................... G01N 27/04

FOREIGN PATENT DOCUMENTS

JP          2001-124716 A     5/2001

* cited by examiner

*Primary Examiner* — Xin Y Zhong
(74) *Attorney, Agent, or Firm* — Sughrue Mion, PLLC

(57) ABSTRACT

Disclosed is a gas sensor for detecting hydrogen gas in a measurement gas atmosphere, including: a first installation part defining a first inner space in communication with the measurement gas atmosphere through a solid electrolyte membrane member; a second installation part defining a second inner space in direct communication with the measurement gas atmosphere; first and second sensor elements respectively installed in the first and second inner spaces; and a calculation unit configured to calculate the concentration of the hydrogen gas according to a potential between the first and second sensor elements. The gas sensor further includes a current detecting portion that detects a current flowing through the first and second sensor elements. The calculation unit is configured to, when the current detected by the current detecting portion is larger than or equal to a threshold value, judge that the hydrogen gas is present at high concentration.

3 Claims, 6 Drawing Sheets

GAS SENSOR

FIELD OF THE INVENTION

The present invention relates to a gas sensor.

BACKGROUND OF THE INVENTION

There is known a gas sensor capable of detecting and measuring hydrogen gas in a measurement gas atmosphere without being influenced by water (humidity) as in, for example, Japanese Laid-Open Patent Publication No. 2001-124716. This gas sensor has a pair of first and second sensor elements installed in first and second separate inner spaces. The first inner space in which the first sensor element (as a reference sensor element) is installed is in communication with the measurement gas atmosphere through a membrane member, whereas the second inner space in which the second sensor element (as a detection sensor element) is installed is open to the measurement gas atmosphere. The membrane member has the property of allowing permeation of water vapor but not allowing permeation of hydrogen gas (as a measurement target gas). In this configuration, both of the first and second sensor elements are placed under the same humidity conditions so as to enable detection and measurement of the measurement target gas without being influenced by humidity.

SUMMARY OF THE INVENTION

Although the membrane member has the property of not allowing permeation of hydrogen gas as mentioned above, it is not possible to completely interrupt permeation of hydrogen gas through the membrane member. In the case where the concentration of hydrogen gas in the measurement gas atmosphere is high, the hydrogen gas passes through the membrane member and enters into the first inner space in which the first sensor element (reference sensor element) is installed. Consequently, the potential difference between the first and second sensor elements becomes small so that the gas sensor outputs a low hydrogen gas concentration signal even though the hydrogen gas is present at high concentration.

In view of the foregoing, it is an object of the present invention to provide a gas sensor capable of accurately judging a high hydrogen gas concentration environment.

In accordance with a first aspect of the present invention, there is provided a gas sensor for detecting hydrogen gas in a measurement gas atmosphere, comprising: first and second sensor elements connected in series to each other so as to form one side of a bridge circuit and each having a resistance value that varies with changes in temperature thereof; a first installation part defining a first inner space in which the first sensor element is installed, the first installation part having formed therein a first gas introduction hole that provides communication between the first inner space and the measurement gas atmosphere through a membrane member of solid polymer electrolyte; a second installation part defining a second inner space in which the second sensor element is installed, the second installation part having formed therein a second gas introduction hole that provides communication between the second inner space and the measurement gas atmosphere without through a membrane member, and a calculation unit configured to calculate the concentration of the hydrogen gas in the measurement gas atmosphere according to a potential between the first and second sensor elements, wherein the gas sensor further comprises a current detecting portion configured to detect a current flowing through the first and second sensor elements; and wherein the calculation unit is configured to, when the current detected by the current detecting portion is larger than or equal to a threshold value, make a judgement that the hydrogen gas is present at high concentration.

In an environment where the hydrogen gas is present at high concentration, the hydrogen gas enters into the first inner space in which the first sensor element (as a reference sensor element) is installed so that the concentration of the hydrogen gas in the first inner space becomes increased. The resistance of the first sensor element is decreased with increase in the concentration of the hydrogen gas in the first inner space. Simultaneously, the resistance of the second sensor element is decreased as the second sensor element is exposed to the hydrogen gas in the second inner space. As a result, the current detected by the current detecting portion becomes large. In the first aspect, the calculating unit is configured to make a judgment that the hydrogen gas is present at high concentration when the current detected by the current detecting portion is larger than or equal to the threshold value. It is therefore possible to judge the presence of the hydrogen gas at high concentration irrespective of the output of the gas sensor.

In accordance with a second aspect of the present invention, there is provided a gas sensor as described above, wherein the calculation unit is configured to make the judgment after a predetermined time has elapsed from a start of voltage application to the first and second sensor elements.

At power-on of the gas sensor, there arises a flow of excessive current between the first and second sensor elements. In the second aspect, the calculation unit is configured to exclude use of such excessive current for the judgment. It is thus possible to improve the accuracy of judgment of the high hydrogen gas concentration environment.

In accordance with a third aspect of the present invention, there is provided a gas sensor as described above, wherein each of the first and second sensor elements is a thermal conductivity type sensor element having a heating resistor whose resistance value varies with changes in temperature thereof.

Some types of sensor elements are known including not only a thermal conductivity type sensor element but also a contact combustion type sensor element that causes combustion of hydrogen gas by the action of a combustion catalyst such as noble metal. In the high hydrogen gas concentration environment, there is a possibility of oxygen depletion. When combustion contact type sensor elements are used as the first and second sensor elements, the current detected by the current detecting portion may become small due to less combustion reaction of hydrogen gas in the high hydrogen gas concentration environment. In the third aspect, however, thermal conductivity type sensor elements are used as the first and second sensor elements so that the current detected by the current detecting portion increases in proportion to the hydrogen gas concentration even in the high hydrogen gas concentration environment where oxygen may become depleted. It is thus possible to accurately judge the presence of the hydrogen gas at high concentration even in the high hydrogen gas concentration environment where oxygen may become depleted.

The other objects and features of the present invention will also become understood from the following description.

DESCRIPTION OF EMBODIMENTS

Hereinafter, an exemplary embodiment of the present invention will be described below with reference to the drawings.

1-1. Embodiment

Figure 1:
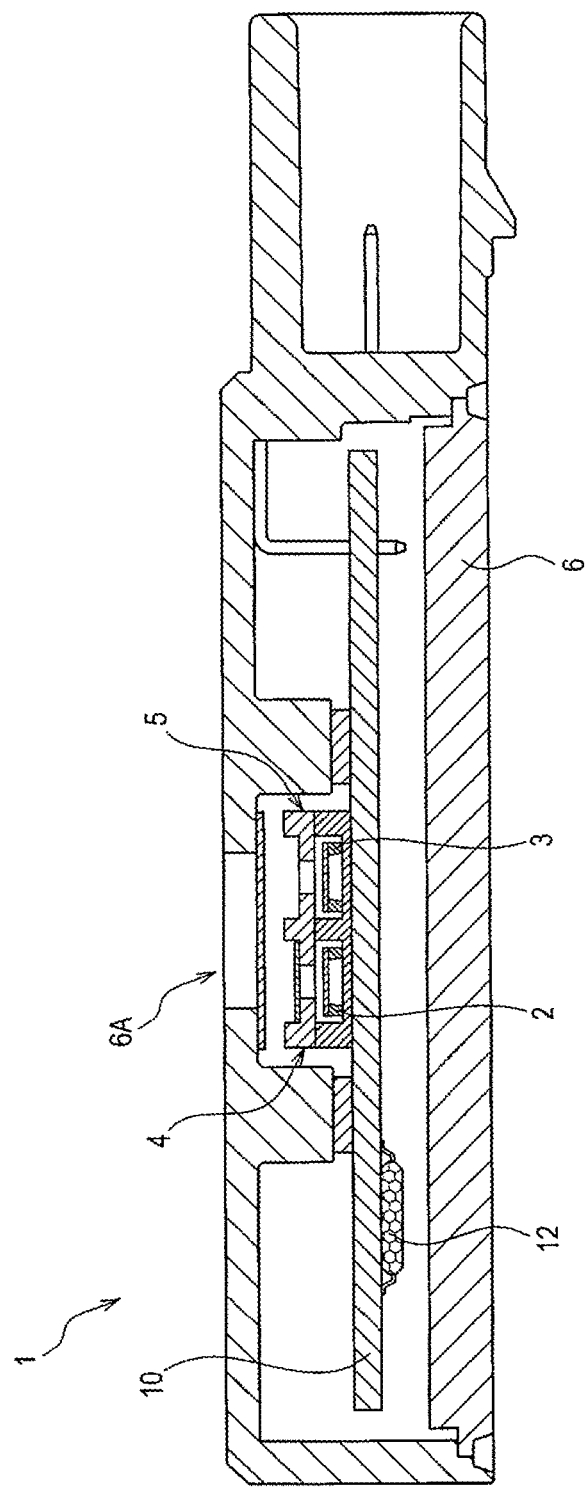
FIG. 1 is a schematic cross-sectional view of a gas sensor according to an embodiment of the present invention.
Figure 2:
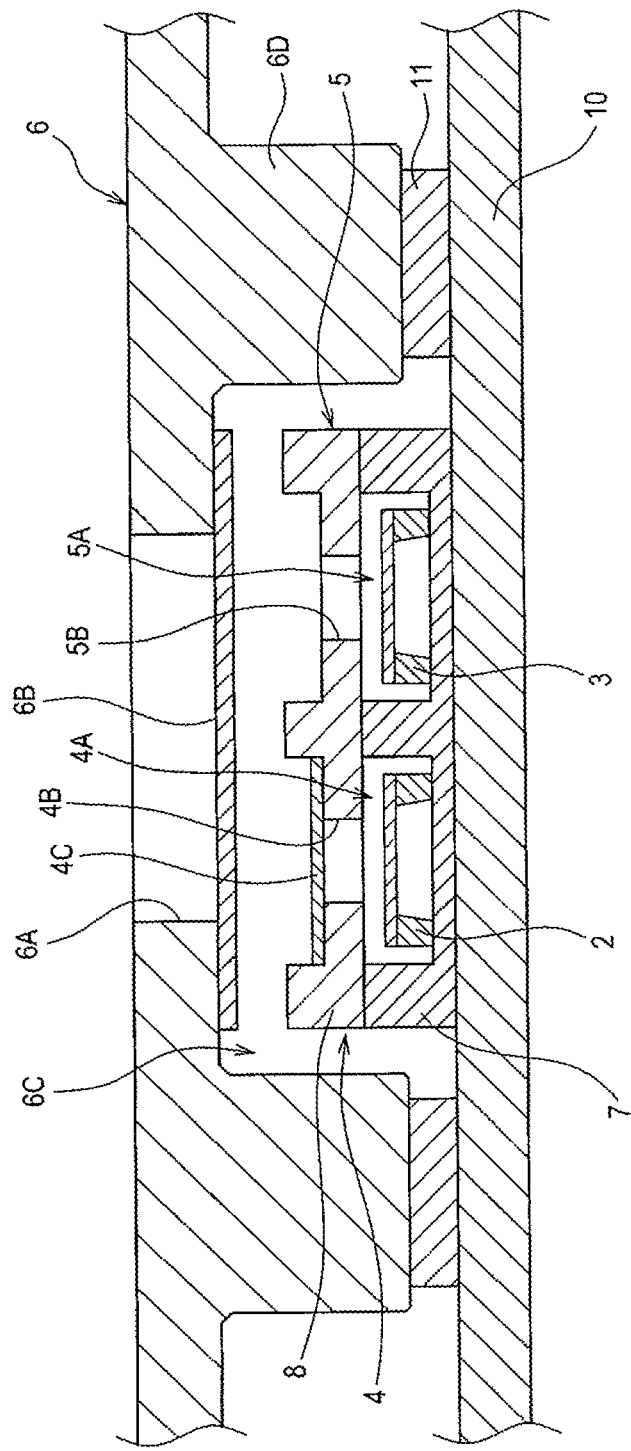
FIG. 2 is an enlarged cross-sectional of a part of the gas sensor in the vicinity of first and second installation parts according to the embodiment of the present invention.

A gas sensor 1 according to one embodiment of the present invention is used to detect and measure hydrogen gas in a measurement gas atmosphere. As shown in FIGS. 1 and 2, the gas sensor 1 includes a first sensor element 2, a second sensor element 3, a first installation part 4, a second installation part 5, a casing 6, a circuit board 10 and a calculation unit 12.

<First and Second Sensor Elements>

Figure 3:
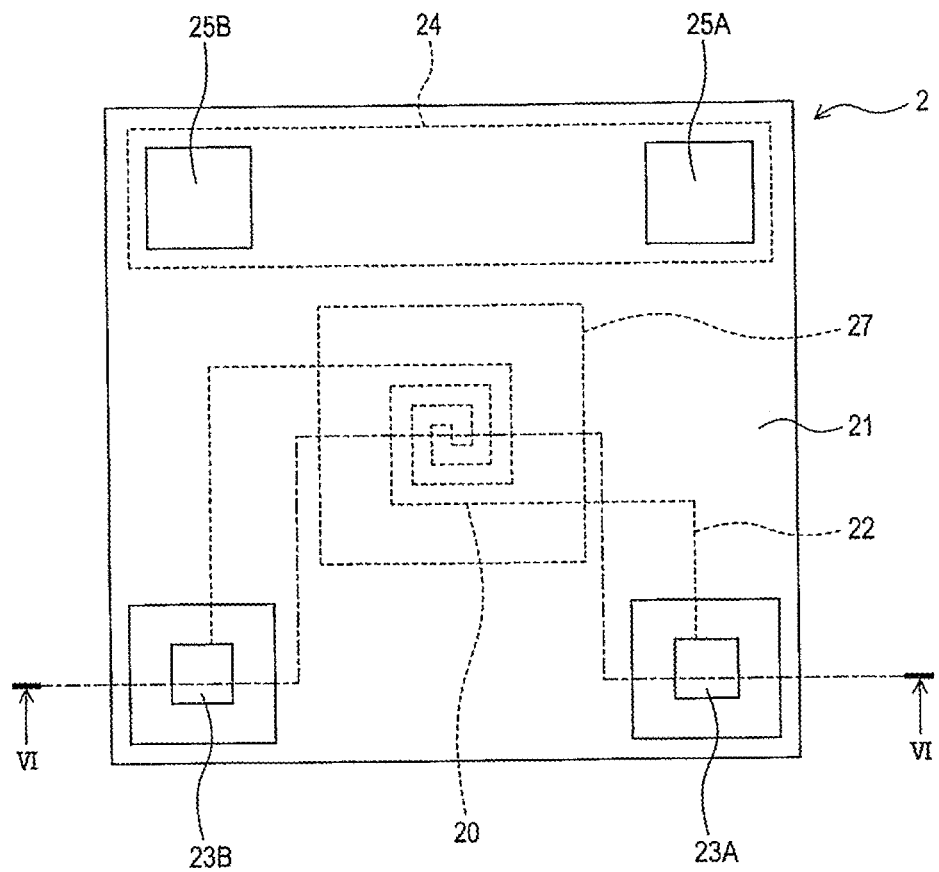
FIG. 3 is a schematic plan view of a sensor element of the gas sensor according to the embodiment of the present invention.
Figure 4:
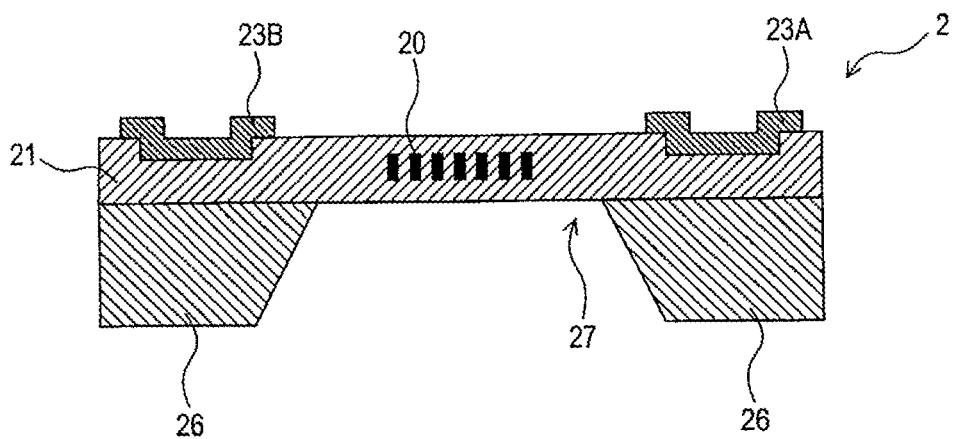
FIG. 4 is a schematic cross-sectional view of the sensor element as taken along line VI-VI of FIG. 3.

The first sensor element 2 is in the form of a thermal conductivity type sensor element having a heating resistor 20 whose resistance value varies with changes in temperature thereof. More specifically, the first sensor element 2 includes a heating resistor 20, an insulating layer 21, a wiring 22, a pair of first electrode pads 23A and 23B, a temperature measuring resistor 24, a pair of second electrode pads 25A and 25B and a substrate 26 as shown in FIGS. 3 and 4.

The heating resistor 20 is provided as a spiral pattern conductor and is embedded in a center portion of the insulating layer 21. Further, the heating resistor 20 is electrically connected to the first electrode pads 23A and 23B via the wiring 22.

The first electrode pads 23A and 23B are disposed on one side of the insulating layer 21. One of the first electrode pads 23A and 23B is connected to a ground, whereas the other of the first electrode pads 23 and 23B is connected to the circuit board 10.

The substrate 26 is made of a silicon material and disposed on the other side of the insulating layer 21. As shown in FIG. 4, a hollow 27 is formed in the substrate 26 at a position corresponding to the heating resistor 20 so as to provide a diaphragm structure with the insulating layer 21 being exposed to the outside through the hollow 27.

The temperature measuring resistor 24 is embedded in a portion of the insulating layer 20 closer to the outer periphery than the heating resistor 20, so as to extend along one side of the insulating layer 21, and is electrically connected to the second electrode pads 25A and 25B.

The second electrode pads 25A and 25B are disposed on the same side of the insulating layer 21 as the first electrode pads 23A and 23B. One of the second electrode pads 25A and 25B is connected to a ground, whereas the other of the first electrode pads 23 and 23B is connected to the circuit board 10.

The heating resistor 20 is made of a conductive material having a high temperature resistance coefficient, and thus has a resistance value that varies with changes in temperature thereof. For example, there can be used platinum (Pt) as the material of the heating resistor 20. The temperature measuring resistor 24 is made of a conductive material whose resistance value varies in proportion to temperature thereof. As the material of the temperature measuring resistor 24, there can be used the same material as that of the heating resistor 20, such as platinum (Pt). The wiring 22, the first electrode pads 23A and 23B and the second electrode pads 25A and 25B can also be made of the same material as the material of the heating resistor 20. The insulating layer 21 may be made of a single insulating material or can be made of different kinds of insulating materials in a multi-layer structure. As the insulating material of the insulating layer 21, there can be used silicon oxide ($SiO_2$), silicon nitride ($Si_3N_4$) or the like.

As in the case of the first sensor element 2, the second sensor element 3 is in the form of a thermal conductivity type sensor element having a heating resistor 30 whose resistance value varies with changes in temperature thereof. Since the second sensor element 3 has the same structure as that of the first sensor element 2 in the present embodiment, a detailed explanation of the structure of the second sensor element 3 will be omitted herefrom.

It is preferable that the resistance value of the heating resistor 21 of the first sensor element 2 is equal to that of the second sensor element 3.

<First and Second Installation Parts>

The first installation part 4 has a first inner space 4A, a first gas introduction hole 4B and a membrane member 4C.

The first inner pace 4A is defined in the first installation part 4 such that the first sensor element 2 is installed in the first inner space 4A. The first gas introduction hole 4B is formed in the first installation part 4 so as to provide communication between the first inner space 4A and the measurement gas atmosphere (that is, the inside of the casing 6 outside the first inner space 4A).

The membrane member 4C is arranged to cover the whole of the first gas introduction hole 4B. Herein, the membrane member 4C is made of a solid polymer electrolyte that allows permeation of water vapor and allows less permeation of hydrogen gas than water vapor (i.e. inhibits permeation of hydrogen gas). The membrane member 4C can preferably be a fluororesin-based ion exchange membrane. Specific examples of the fluororesin-based ion exchange membrane usable as the membrane member 4C are those available under the trade names of Nafion, Flemion, Aciplex and the like. Alternatively, the membrane member 4C may be a hollow fiber membrane capable of separating the measurement target gas and water vapor from each other.

Accordingly, the flow of the measurement target gas into the first inner space 4A is prevented by the membrane member 4C. The first sensor element 2 installed in the first inner space 4A serves as a reference sensor electrode without being exposed to the measurement target gas. The first sensor element 2 is however placed under the same humidity conditions as the second sensor element 3 because water vapor passes through the membrane member 4C.

The first installation part 4 has no opening other than the first gas introduction hole 4B.

On the other hand, the second installation part 5 has a second inner space 5A and a second gas introduction hole 5B.

The second inner pace 5A is defined in the second installation part 5 such that the second sensor element 3 is installed in the second inner space 5A. The second gas introduction hole 5B is formed in the second installation part 5 so as to provide communication between the second inner space 5A and the measurement gas atmosphere (that is, the inside of the casing 6 outside the second inner space 5A).

As the second gas introduction hole 5B is not covered by a membrane member and is open to the measurement gas atmosphere, the measurement target gas is introduced from the inside of the casing 6 into the second inner space 5A through the second gas introduction hole 5B. In other words, the second gas introduction hole 5A enables direct introduction of the measurement target gas into the second inner space 5A without through a membrane member.

The second installation part 5 also has no opening other than the second gas introduction hole 5B.

In the present embodiment, the first and second installation parts 4 and 5 are constituted by a common mount base 7 and a common protective cap (or cover) 8 as shown in FIGS. 1 and 2. Namely, the first and second inner spaces 4A and 5A are separately and adjacently defined, with a partition wall formed therebetween, by mounting the protective cap 8 on the mount base 7. As the first and second inner spaces 4A and 5A are located adjacent to each other, the difference in temperature between the first and second inner spaces 4A and 5A can be reduced so as to decrease output variations of the gas sensor 1 with respect to temperature changes and thereby reduce an error in the output of the gas sensor 1.

The mount base 7 is disposed on a surface of the circuit board 10 and is formed with two recess portions in which the first and second sensor elements 2 and 3 are respectively mounted.

The protective cap 8 is bonded to the mount base 7 so as to cover the mount base 7 as well as the first and second sensor elements 2 and 3 mounted in the recess portions of the mount base 7. Further, the first and second gas introduction holes 4B and 5B are formed through the protective cap 8.

The mount base 7 is made of an insulating ceramic material. Example of the insulating ceramic material suitably usable as the material of the mount base 7 are alumina, aluminum nitride, zirconia and the like. The protective cap 8 is also made of an insulating ceramic material. Example of the insulating ceramic material suitably usable as the material of the protective cap 8 are alumina and the like. In the present embodiment, the mount base 7 and the protective cap 8 are made of the same insulating ceramic material.

In the present embodiment, the mount base 7 and the protective cap 8 are bonded together by an insulating adhesive 9A. The insulating adhesive 9A can be an insulating adhesive containing a thermosetting resin, thermoplastic resin, ultraviolet curable resin or the like as a main component. For improvement of adhesion between the mount base 7 and the protective cap 8, it is preferable to use an insulating adhesive containing a thermosetting resin as a main component. Specific examples of the thermosetting resin usable in the insulating adhesive are epoxy resin and polyolefin resin. The expression "main component" as used herein means a component contained in an amount of 80 mass % or more.

The membrane member 4C is disposed in a recess portion of the protective cap 8 and is bonded and sealed at a periphery thereof to the protective cap 8 by an adhesive. As the membrane member 4C is situated to cover an opening of the first gas introduction hole 4B from the outside of the first inner space 4A, it is feasible to arrange the membrane member 4C after defining the first inner space 4A by reflowing of the base 7 and the protective cap 8, whereby the membrane member 4C can be prevented from deformation due to expansion of air in the first inner space 4A during the reflowing. Alternatively, the membrane member 4C may be situated to cover the first gas introduction hole 4B from the first inner space 4A side.

<Casing>

The casing 6 is adapted to accommodate therein the first and second installation parts 4 and 5. The casing 6 has: a casing body formed with an opening 6A for introduction of the measurement target gas into the inside of the casing 6; and a filter 6B arranged in the opening 6A.

More specifically, the casing 6 includes an inner frame portion 6D protruding inward from an inner surface of the casing body as shown in FIG. 2. As the circuit board 10 is fixed to the inner frame portion 6D of the casing 6 via a seal member 11, there is an inner space 6C defined between the casing 6 and the circuit board 10. The first and second installation parts 4 and 5 (that is, the mount base 7 and the protective cap 8) are accommodated in this inner space 6C.

The opening 6A is formed in the casing body so as to provide communication between the measurement gas atmosphere and the inner space 6C and introduce the measurement target gas into the inner space 6C. The measurement target gas introduced into the inner space 6C is supplied only to the second inner space 5A through the second gas introduction hole 5B. On the other hand, water vapor in the inner space 6C is diffused into both of first and second inner spaces 4A and 5A.

The filter 6B is in the form of a water-repellent filter that allows permeation of the measurement target gas but does not allow permeation of water in liquid form (i.e. removes water drop contained in the measurement target gas). By the arrangement of such a water-repellent filter 6B, the entry of water drop and other foreign substance into the inner space 6C can be prevented. In the present embodiment, the filter 6B is attached to the inner surface of the casing 6 so as to cover the opening 6A.

<Circuit Board>

The circuit board 10 is plate-shaped and disposed inside the casing 6. The circuit board 10 has a circuit system configured as shown in FIG. 5 and electrically connected to the respective electrode pads 23A, 23B, 25A and 25B of the sensor elements 2 and 3.

Figure 5:
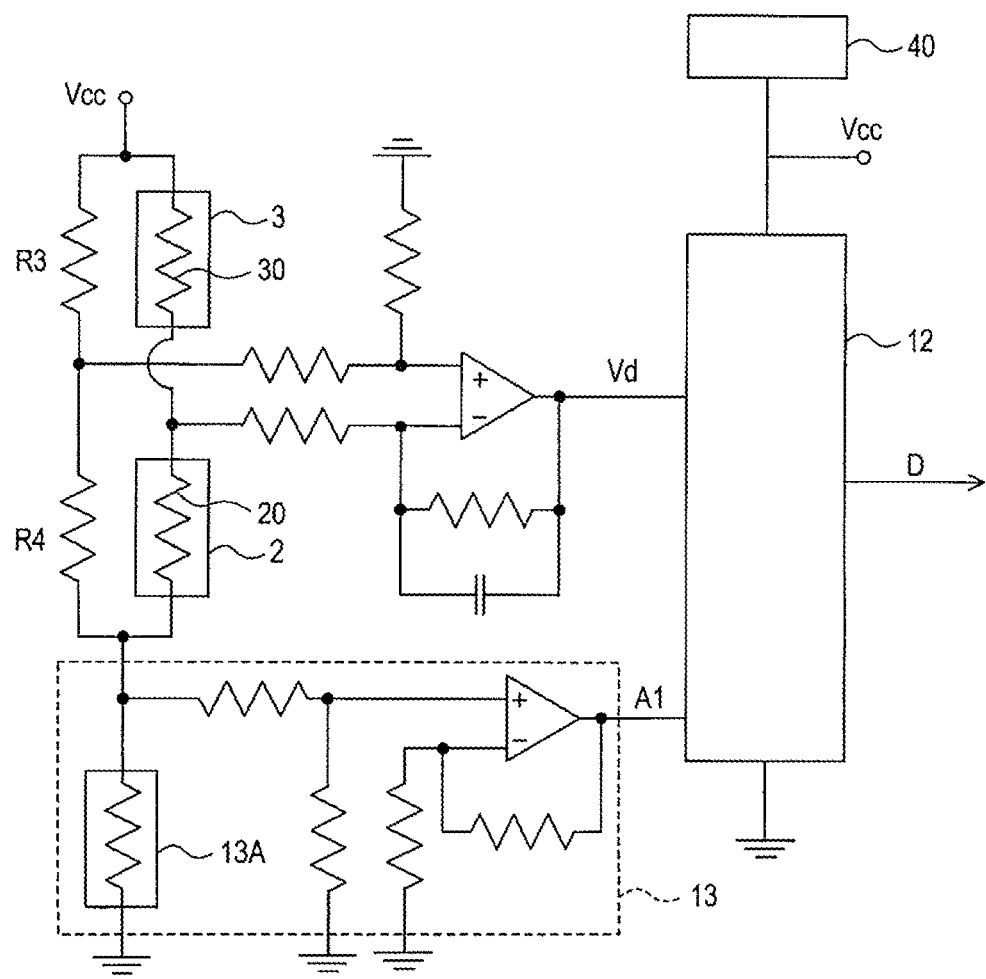
FIG. 5 is a schematic circuit diagram of the gas sensor according to the embodiment of the present invention.

As shown in FIG. 5, the circuit board 10 (circuit system) includes a current detecting portion 13 that detects a current flowing through the first and second sensor elements 2 and 3 in the present embodiment. Herein, the first and second sensor elements 2 and 3 are connected in series to each other, and fixed resistors R3 and the R4 connected in series to each other in the circuit system of the circuit board 10. The series-connected sensor elements 2 and 3 and the series-connected resistors R3 and R4 are arranged in parallel with each other so as to form a bridge circuit. Further, the current detecting portion 13 has a shunt resistor 13A connected in series to the bridge circuit so as to read a current in the bridge circuit and convert the read current to a voltage. As the bridge circuit has one side formed by the first and second sensor elements 2 and 3 (whose resistance values vary with changes in temperature thereof) and the other side formed by the fixed resistors R3 and R4 (whose resistance values are fixed) as mentioned above, the reading of current change in the bridge circuit corresponds to the reading of current change in the first and second sensor elements 2 and 3. The thus-obtained voltage is amplified by a voltage amplifier of the current detection portion 13 and outputted as a current detection voltage A1 to the calculation unit 12.

<Calculation Unit>

The calculation unit 12 is configured to calculate the concentration D of hydrogen gas in the measurement gas atmosphere according to a potential between the heating resistors 20 and 30 of the first and second sensor elements 2 and 3 under the application of a constant voltage Vcc to the heating resistors 20 and 30. With the application of a constant voltage Vcc between the heating resistors 20 and 30, there develop a potential between the heating resistors 20 and 30 and a potential between the fixed resistors R3 and R4. A difference between these potentials is amplified by a differential amplifier of the circuit board 10 and outputted as a potential difference Vd to the calculation unit 12. Then, the concentration D of the measurement target gas is calculated based on the potential difference Vd and outputted by the calculation unit 12.

The calculation unit 12 and the circuit board 10 are supplied with current from a direct-current power supply 40. Further, the voltage is applied to the heating resistors 20 and 30 of the first and second sensor elements 2 and 3 from the direct-current power supply 40.

In the present embodiment, the calculation unit 12 is also configured to make a judgement that the hydrogen gas is present at high concentration when the current detected by the current detecting portion 13 is larger than or equal to a predetermined threshold value.

More specifically, the calculation unit 12 judges that the hydrogen gas is present at high concentration when the current detection voltage A1 outputted from the current detecting portion 13 is higher than or equal to a predetermined threshold value A0 (A≥A0). The threshold value A0 is previously determined according to the specifications of the gas sensor 1, the assumed range of the hydrogen gas concentration value D and the like, and is stored in the calculation unit 12. Since the current detection voltage A1 outputted from the current detecting portion 13 is a value obtained by amplification of the voltage detected by the shunt resistor 13, the threshold value A0 is determined relative to the amplified current detection voltage value A1.

When judging that the hydrogen gas is present at high concentration, the calculation unit 12 outputs a signal notifying the presence of the hydrogen gas at high concentration. This signal can be outputted as a special signal indicating the high concentration of the hydrogen gas or as a signal indicating an upper limit value or abnormal value of the hydrogen gas concentration D.

Furthermore, the calculation unit 12 makes the above high hydrogen gas concentration judgment after the lapse of a predetermined standby time t0 from a start of voltage application to the first and second sensor elements 2 and 3 (heating resistors 20 and 30). The standby time t0 is determined as a time from start of energization of the heating resistors 20 and 30 to stabilization of the energization states of the heating resistors 20 and 30. In other words, the standby time t0 corresponds to a time during which the resistance values of the respective heating resistors 20 and 30 fall within a given resistance range after the start of voltage application to the first and second sensor elements 2 and 3 in the environment where the hydrogen gas is not present at high concentration.

1-2. Judgment Process

Figure 6:
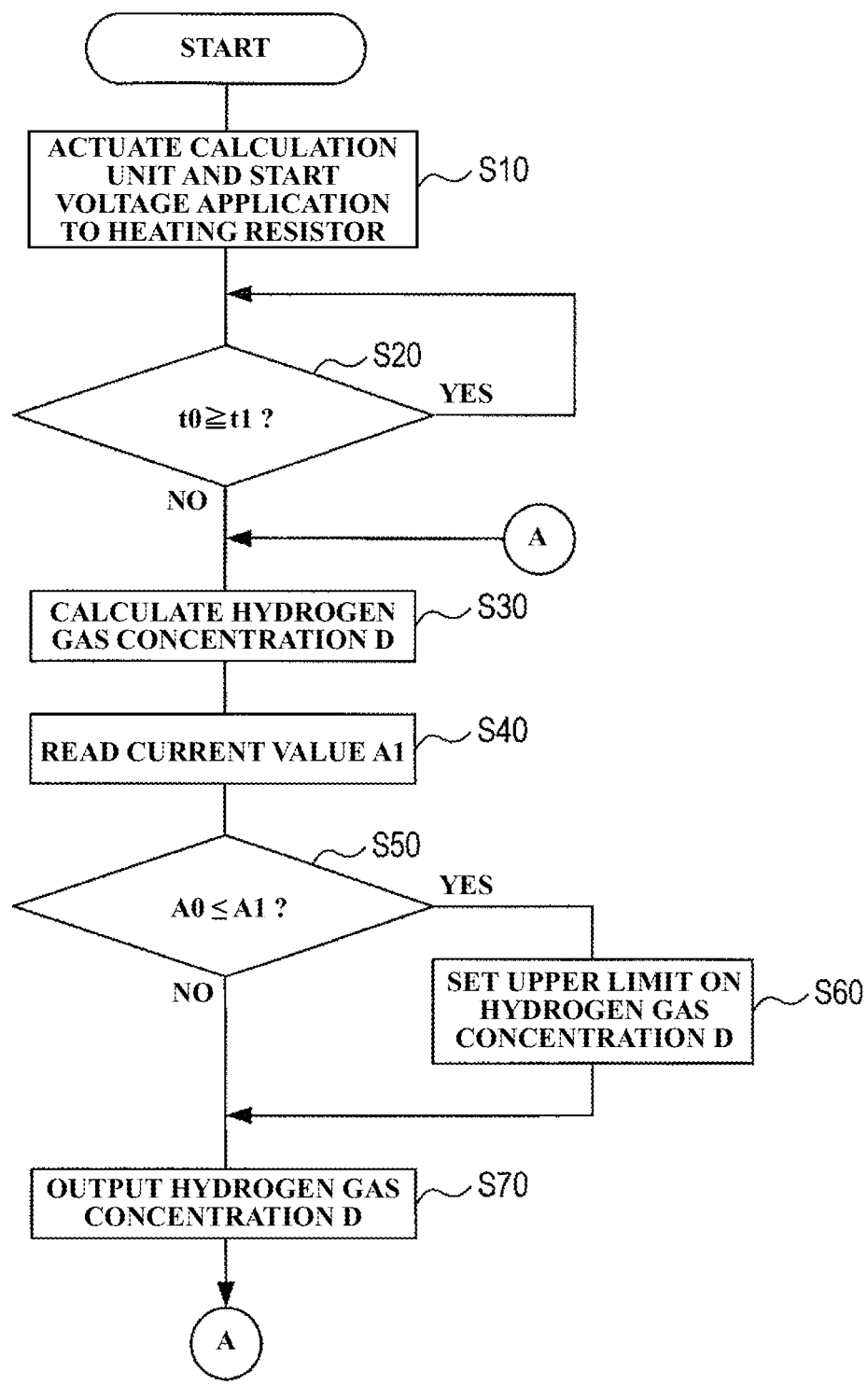
FIG. 6 is a flowchart of a judgment process executed by a calculation unit of the gas sensor according to the embodiment of the present invention.

A judgment process executed by the calculation unit 12 of the gas sensor 1 will be now explained in more detail below with reference to FIG. 6.

In step 10, the calculation unit 12 is actuated upon supply of power to the gas sensor 1; and the application of voltage to the heating resistors 20 and 30 of the first and second sensor elements 2 and 3 is started.

In step S20, the calculation unit 12 compares the predetermined standby time t0 with an elapsed time t1 from the start of voltage application to the first and second sensor elements 2 and 3 and judges whether the standby time t0 is longer than or equal to the elapsed time t1. When t0≥t1 (YES in step S20), the calculation unit 12 repeats the processing of step 12 until the standby time t0 becomes shorter than the elapsed time t1. When t0<t1 (NO in step S20), the calculation unit 12 proceeds to step S30.

In step S30, the calculation unit 12 calculates the hydrogen gas concentration D according to the potential between the first and second sensor elements 2 and 3.

After that, the calculation unit 12 reads the current detection voltage A1 from the current detecting portion 13 of the circuit board 10 in step S40. As mentioned above, the current detection voltage A1 corresponds to the current flowing through the first and second sensor elements 2 and 3.

In step S50, the calculation unit 12 compares the current detection voltage A1 with the predetermined threshold value A0 and judges whether the threshold value A0 is lower than or equal to the current detection voltage A1. When A0≤A1 (YES in step S50), the calculation unit 12 proceeds to step S60. When A0>A1 (NO in step S50), the calculation unit 12 proceeds to step S70.

In step S60, the calculation unit 12 judges that the hydrogen gas is present at high concentration, and then, sets an upper limit on the hydrogen gas concentration D (i.e. overwrites the hydrogen gas concentration D with its upper limit value). Then, the calculation unit 12 proceeds from step S60 to step S70.

In step S70, the calculation unit 12 outputs the hydrogen gas concentration D. Namely, the calculated value of the hydrogen gas concentration D obtained in step S30 is outputted as it is when A0>A1; and, when A0≤A1, the upper limit value of the hydrogen gas concentration D set in step S60 is outputted to notify the presence of the hydrogen gas at high concentration.

As mentioned above, the calculation unit 12 may output a special signal indicating the high concentration of the hydrogen gas instead of setting the upper limit on the hydrogen gas concentration value D in step S60. In this case, the calculation unit 12 may not perform the processing of step S70.

After outputting the hydrogen gas concentration D in step S70, the calculation unit 12 proceeds back to step S30 and repeats the processing of steps S30 to S70 until power shutdown of the gas sensor 1.

1-3. Effects

The following effects are obtained in the present embodiment.

(1a) The calculation unit 12 is configured to judge that the hydrogen gas is present at high concentration when the current detected by the current detecting portion 13 is larger than or equal to the predetermined value. It is therefore possible to judge the presence of the hydrogen gas at high concentration irrespective of the output of the gas sensor 1.

(1b) At power-on of the gas sensor 1, there arises a flow of excessive current between the first and second sensor elements 2 and 3. By the processing of step S20, however, such excessive current is excluded from use for judgment of the high hydrogen gas concentration atmosphere. It is thus possible to improve the accuracy of judgment of the high hydrogen gas concentration environment.

(1c) The thermal conductivity type sensor elements, in each of which the resistance value of the heating resistor 20, 30 varies with changes in temperature thereof, are used as the first and second sensor elements 2 and 3. By the use of such sensor elements 2 and 3, the current detected by the current detecting portion 13 increases in proportion to the hydrogen gas concentration even in the high hydrogen gas concentration environment where oxygen may become depleted. It is thus possible to accurately judge the presence of the hydrogen gas at high concentration even in the high hydrogen gas concentration environment where oxygen may become depleted.

2. Modification Examples

Although the present invention has been described with reference to the above embodiment, the above embodiment is intended to facilitate understanding of the present invention and is not intended to limit the present invention thereto. Various changes and modifications can be made to the above embodiment without departing from the scope of the present invention.

Figure 7:
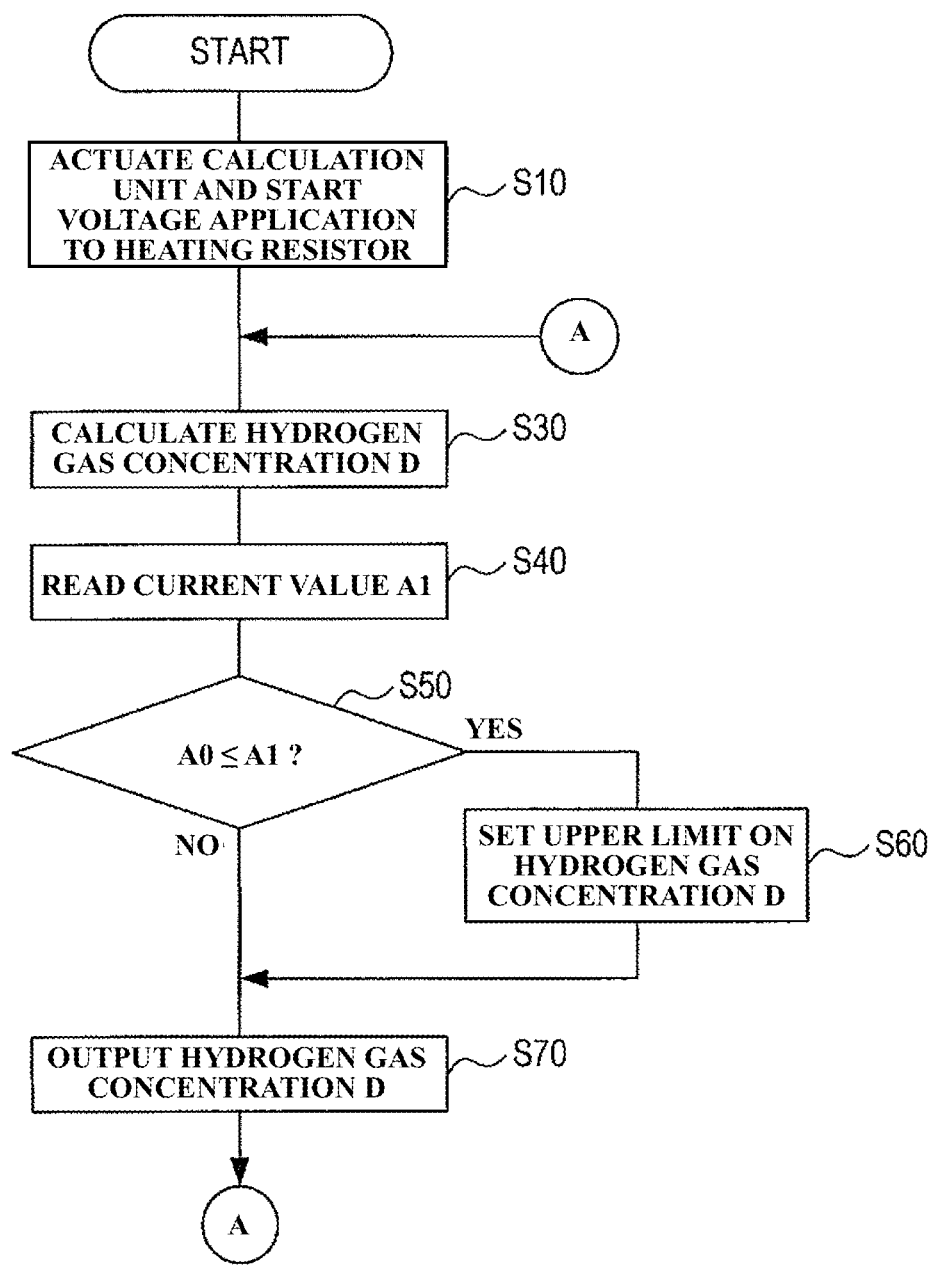
FIG. 7 is a flowchart of a judgment process executed by a calculation unit of a gas sensor according to a modification of the embodiment of the present invention.

(2a) The calculation unit 12 does not necessarily make After the lapse of the predetermined time from the start of voltage application to the first and second sensor elements 2 and 3. A shown in FIG. 7, it is feasible to perform the processing of steps S30 to 70 (the calculation of the hydrogen gas concentration D and the judgment about the presence of the hydrogen gas at high concentration) immediately after the actuation of the calculation unit 12 in step S10.

(2b) The above-mentioned structures of the first and second installation parts 4 and 5 are merely an example. The first and second installation parts 4 and 5 may alternatively be formed as separate parts by providing the mount base 7 and protective cap 8 for the first installation part 4 separately from those for the second installation part 5. The first and second installation parts 4 and 5 may be located apart from each other. Each of the first and second installation parts 4 and 5 is not necessarily formed by the mount base 7 and the protective cap 8 and may be formed by a single hollow structural member.

(2c) In the gas sensor 1, each of the first and second sensor elements 2 and 4 may not be equipped with the temperature measuring resistor 24. Alternatively, the first and second installation parts 4 and 5 may be each provided with any temperature measuring means other than the temperature measuring resistor 24.

(2d) In the above embodiment, it is feasible to divide the function of one component among a plurality of components or combine the functions of a plurality of components into one. Any of the technical features of the above embodiments may be omitted, replaced or combined as appropriate. All of embodiments and modifications derived from the technical scope of the following claims are included in the present invention.

The entire contents of Japanese Patent Application No. 2017-177554 (filed on Sep. 15, 2017) and No. 2018-078996 (filed on Apr. 17, 2018) are herein incorporated by reference.

What is claimed is:

1. A gas sensor for detecting hydrogen gas in a measurement gas atmosphere, comprising:
   first and second sensor elements connected in series to each other so as to form one side of a bridge circuit and each having a resistance value that varies with changes in temperature thereof;
   a first installation part defining a first inner space in which the first sensor element is installed, the first installation part having formed therein a first gas introduction hole that provides communication between the first inner space and the measurement gas atmosphere through a membrane member of solid polymer electrolyte;
   a second installation part defining a second inner space in which the second sensor element is installed, the second installation part having formed therein a second gas introduction hole that provides communication between the second inner space and the measurement gas atmosphere without through a membrane member; and
   a calculation unit configured to calculate a concentration of the hydrogen gas in the measurement gas atmosphere according to a potential between the first and second sensor elements,
   wherein the gas sensor further comprises a current detecting portion configured to detect a current flowing through the first and second sensor elements; and
   wherein the calculation unit is configured to, when the current detected by the current detecting portion is larger than or equal to a threshold value, make a judgement that the hydrogen gas is present at a concentration higher than or equal to a predetermined concentration.

2. The gas sensor according to claim 1,
   wherein the calculation unit is configured to make said judgment after a predetermined time has elapsed from a start of voltage application to the first and second sensor elements.

3. The gas sensor according to claim 1,
   wherein each of the first and second sensor elements is a thermal conductivity type sensor element having a heating resistor whose resistance value varies with changes in temperature thereof.

* * * * *